US012728258B2

(12) United States Patent
Chung et al.

(10) Patent No.: US 12,728,258 B2
(45) Date of Patent: Sep. 8, 2026

(54) DEVICE FOR REGENERATING NERVE CELLS AND SUPPRESSING IMMUNE DISEASES

(71) Applicant: SAMSUNG LIFE PUBLIC WELFARE FOUNDATION, Seoul (KR)

(72) Inventors: Tae Young Chung, Seongnam-si (KR); Dong Hui Lim, Seoul (KR); Young Sik Yoo, Seoul (KR); Do Hyoung Kim, Seoul (KR); Pyung Kyu Kim, Incheon (KR); Young Min Park, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 284 days.

(21) Appl. No.: 18/278,898

(22) PCT Filed: Feb. 14, 2022

(86) PCT No.: PCT/KR2022/002141
§ 371 (c)(1),
(2) Date: Aug. 25, 2023

(87) PCT Pub. No.: WO2022/182037
PCT Pub. Date: Sep. 1, 2022

(65) Prior Publication Data

US 2024/0131323 A1 Apr. 25, 2024
US 2024/0226536 A9 Jul. 11, 2024

(30) Foreign Application Priority Data

Feb. 26, 2021 (KR) ........................ 10-2021-0026457

(51) Int. Cl.
*A61N 1/04* (2006.01)
*A61N 1/36* (2006.01)

(52) U.S. Cl.
CPC ....... *A61N 1/0456* (2013.01); *A61N 1/36046* (2013.01)

(58) Field of Classification Search
CPC .............. A61N 1/0456; A61N 1/36046; A61N 1/0476; A61N 1/0484; A61N 1/32;
(Continued)

(56) References Cited

U.S. PATENT DOCUMENTS 10,695,566 B1 * 6/2020 Kim .................... A61N 1/3603
2008/0208335 A1 * 8/2008 Blum .................... G02B 1/043
623/6.22
(Continued)

FOREIGN PATENT DOCUMENTS

JP 5704804 B2 4/2015
JP 2018-041070 A 3/2018
(Continued)

OTHER PUBLICATIONS

International Search Report of WIPO in Application No. PCT/KR2022/002141, filed Feb. 14, 2022.

*Primary Examiner* — Mallika D Fairchild
(74) *Attorney, Agent, or Firm* — DILWORTH IP, LLC

(57) ABSTRACT

The present invention relates to a device for regenerating nerve cells and suppressing immune diseases, and more particularly, to a device for regenerating nerve cells and suppressing immune diseases, which uses a contact lens containing a conductive material to increase the effect of microcurrent on nerve cell regeneration and immune response suppression. The device for regenerating nerve cells and suppressing immune diseases comprises: a contact lens comprising a body configured to be worn on a cornea, and a conductive material inserted into the body and serving to induce a microcurrent generated outside the body; a plurality of channels configured to come into close contact with skins around eyes and to generate a flow of microcur-
(Continued)

rent on upper part of the contact lens; and a signal supply unit configured to supply electrical signals to the plurality of channels.

8 Claims, 6 Drawing Sheets

(58) Field of Classification Search
CPC . A61N 1/326; A61N 1/36; A61N 1/04; A61N 1/0464; A61N 1/0472; A61N 1/36034; A61F 9/00; A61F 9/0017
See application file for complete search history.

(56) References Cited

U.S. PATENT DOCUMENTS

2011/0157544 A1* 6/2011 Pugh ................ B29D 11/00038 351/158
2018/0154130 A1* 6/2018 Maijer ................... A61N 1/326
2019/0344076 A1* 11/2019 Irazoqui ................... G02C 7/04

FOREIGN PATENT DOCUMENTS

KR 10-1678827 B1 11/2016
KR 10-2064546 B1 1/2020
KR 10-2064547 B1 1/2020

* cited by examiner

DEVICE FOR REGENERATING NERVE CELLS AND SUPPRESSING IMMUNE DISEASES

TECHNICAL FIELD

The present invention relates to a device for regenerating nerve cells and suppressing immune diseases, and more particularly, to a device for regenerating nerve cells and suppressing immune diseases using a contact lens containing a conductive material to increase the effect of microcurrent on nerve cell regeneration and immune response suppression.

BACKGROUND ART

Nerve growth factor (NGF) is an important protein substance for survival, maintenance and growth. In the case of the cornea, nerve growth factor is secreted from the corneal epithelium and plays an important role in the differentiation and maintaining function of peripheral nerves distributed in corneal tissue.

Particularly, when corneal epithelial cells are damaged by vision correction surgery, corneal transplantation surgery, or the like, the corneal epithelial cells induce regeneration of the corneal nerve by increasing the expression of NGF. In addition, NGF is a major factor that activates the immune system, and a decrease in this factor may lead to the occurrence of an unwanted chronic immune disease or the like.

If NGF is not properly expressed due to damage of corneal epithelial cells by vision correction surgery, corneal transplantation surgery, or the like, nerve cells may decrease, causing side effects such as dry eye syndrome or corneal pain, and a chronic immune disease may occur due to the transplanted cornea.

Korean Patent No. 10-2064546 (registered on Jan. 3, 2020; entitled "Multi-channel stimulation system for regenerating damaged corneal nerves") discloses a multi-channel stimulation system for regenerating damaged corneal nerves that is capable of effectively regenerating corneal nerves by applying microcurrent, but does not disclose means for regenerating nerve cells and suppressing chronic immune diseases by increasing NGF expression through the application of microcurrent and for more effectively applying microcurrent to the cornea

DISCLOSURE

Technical Problem

In order to solve the above-described problems, the present invention is to provide a device for regenerating nerve cells and suppressing immune diseases, which increases the effects of the regeneration of corneal nerves and the suppression of immune responses by allowing sufficient amount of microcurrent to be applied to a wearing part of a contact lens containing a conductive material.

Technical Solution

According to one embodiment of the present invention, there is provided a device for regenerating nerve cells and suppressing immune diseases.

The device for regenerating nerve cells and suppressing immune diseases according to one embodiment of the present invention may comprise a contact lens comprising a body configured to be worn on a cornea, and a conductive material inserted into the body and serving to induce a microcurrent generated outside the body, a plurality of channels configured to come into close contact with skins around eyes and to generate a flow of microcurrent on upper part of the contact lens, and a signal supply unit configured to supply electrical signals to the plurality of channels.

In the device for regenerating nerve cells and suppressing immune diseases according to one embodiment of the present invention, the conductive material may be composed of a plurality of conductive fibers, and the conductive fibers may be in partial contact with each other.

In the device for regenerating nerve cells and suppressing immune diseases according to one embodiment of the present invention, the plurality of channels may comprise first and third channels configured to be disposed above user's eyes, and second and fourth channels configured to be disposed under the user's eyes. And electrical signals that are supplied to the first and third channels may be different from electrical signals that are supplied to the second and fourth channels.

In the device for regenerating nerve cells and suppressing immune diseases according to one embodiment of the present invention, the electrical signals may be standardized pulse signals.

In the device for regenerating nerve cells and suppressing immune diseases according to one embodiment of the present invention, the standardized pulse signals may be pulse waves that are applied at intervals of 500 ms.

Advantageous Effects

According to the present invention, it is possible to increase the expression of NGF by more effectively applying microcurrent to the cornea, thereby regenerating nerve cells and suppressing chronic immune diseases.

Effects obtainable in the present disclosure are not limited to the effects mentioned above, and other effects not mentioned herein will be clearly understood by those skilled in the art from the following description.

BEST MODE

Figure 1:
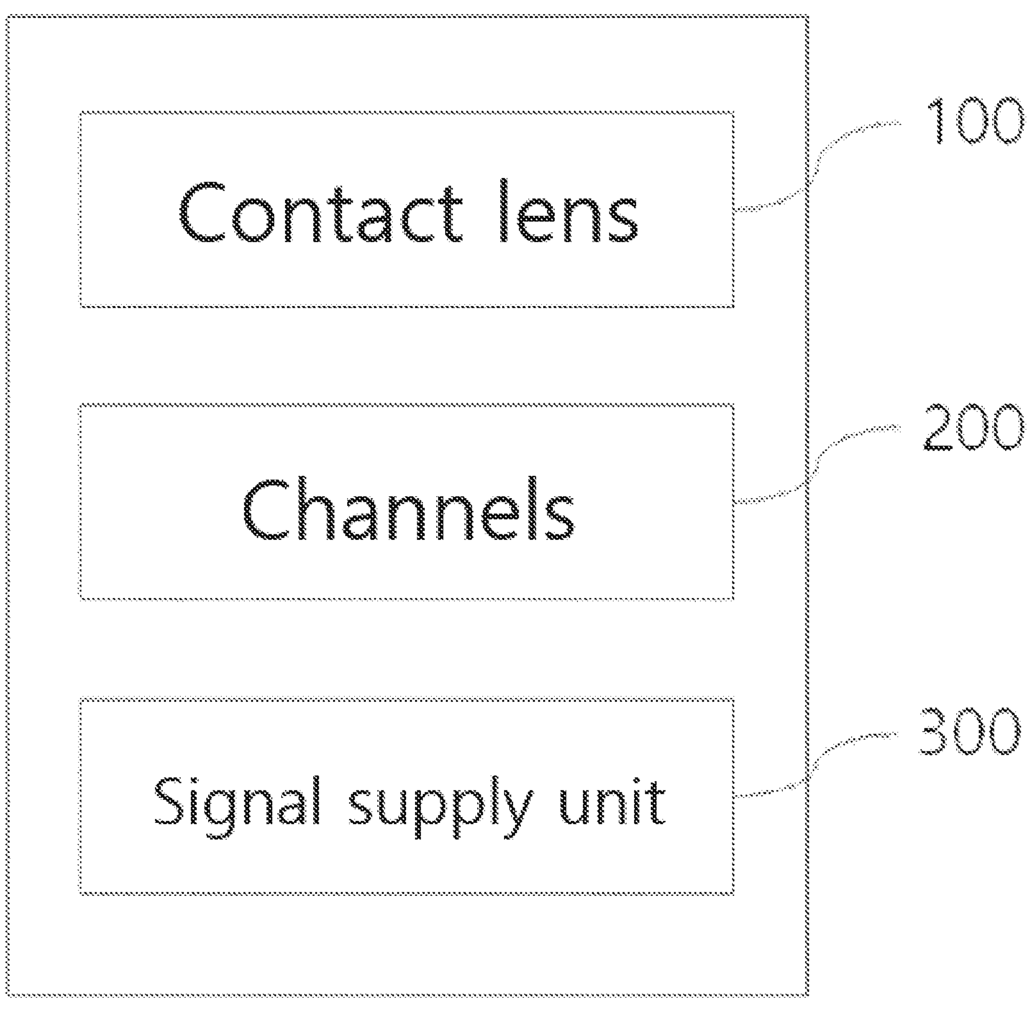
FIG. 1 is a block diagram of a device for regenerating nerve cells and suppressing immune diseases according to one embodiment of the present invention.

According to one embodiment of the present invention, there is provided a device for regenerating nerve cells and suppressing immune diseases.

The device for regenerating nerve cells and suppressing immune diseases according to one embodiment of the present invention may comprise a contact lens comprising a body configured to be worn on a cornea, and a conductive material inserted into the body and serving to induce a microcurrent generated outside the body, a plurality of channels configured to come into close contact with skins around eyes and to generate a flow of microcurrent on upper part of the contact lens, and a signal supply unit configured to supply electrical signals to the plurality of channels.

In the device for regenerating nerve cells and suppressing immune diseases according to one embodiment of the present invention, the conductive material may be composed of a plurality of conductive fibers, and the conductive fibers may be in partial contact with each other.

In the device for regenerating nerve cells and suppressing immune diseases according to one embodiment of the present invention, the plurality of channels may comprise first and third channels configured to be disposed above user's eyes, and second and fourth channels configured to be disposed under the user's eyes. And electrical signals that are supplied to the first and third channels may be different from electrical signals that are supplied to the second and fourth channels.

In the device for regenerating nerve cells and suppressing immune diseases according to one embodiment of the present invention, the electrical signals may be standardized pulse signals.

In the device for regenerating nerve cells and suppressing immune diseases according to one embodiment of the present invention, the standardized pulse signal may be pulse waves that are applied at intervals of 500 ms.

MODE FOR INVENTION

Hereinafter, embodiments of the present invention will be described in detail with reference to the accompanying drawings so that they can be easily carried out by those skilled in the art to which the present invention pertains. However, the present invention may be embodied in various different forms and is not limited to the embodiments described herein. In addition, in the drawings, parts irrelevant to the description are omitted in order to clearly explain the present invention, and like reference numerals denote like parts throughout the specification.

The terms used in the present specification will be briefly described, and the present invention will be described in detail.

The terms used in the present invention are currently widely used general terms selected in consideration of their functions in the present invention, but they may change depending on the intents of those skilled in the art, precedents, or the advents of new technology. In addition, in certain cases, there may be terms arbitrarily selected by the applicant, and in this case, their meanings are described in detail in a corresponding description part of the present invention. Accordingly, terms used in the present disclosure should be defined based on the meaning of the term and the entire contents of the present invention, rather than the simple term name.

Throughout the present specification, it is to be understood that when any part is referred to as "including" any component, it does not exclude other components, but may further include other components, unless otherwise specified. In addition, terms such as " . . . unit" and "module" described in the specification mean a unit that processes at least one function or operation, which may be implemented in hardware or software or a combination of hardware and software. In addition, throughout the present specification, it is to be understood that when any part is referred to as being "connected" to another part, it may be connected "directly" to the other part or "intervening elements" may be present.

Hereinafter, the present invention will be described in detail with reference to the accompanying drawings.

FIG. 1 is a block diagram of a device for regenerating nerve cells and suppressing immune diseases according to one embodiment of the present invention.

Referring to FIG. 1, the device for regenerating nerve cells and suppressing immune diseases according to one embodiment of the present invention may comprise a contact lens 100, a plurality of channels 200, and a signal supply unit 300.

The signal supply unit 300 supplies electrical signals to the plurality of channels 200.

The electrical signals may be standardized pulse signals. The standardized pulse signals may be pulse waves that are applied at intervals of 500 ms (milliseconds). For example, 505 μs biphasic pulse waves having a size between a minimum of 4 mA and a maximum of 16 mA may be applied at an interval of 500 ms for 30 minutes per application.

According to an embodiment, the signal supply unit 300 may further comprise an input unit configured to receive a command of supplying electric signals to the channel 200, a control unit configured to transmit the received command to the signal supply unit 300, a communication unit for communication with the outside, and a charging unit.

The plurality of channels 200 receive electrical signals from the signal supply unit 300 and generate a flow of microcurrent on upper part of the contact lens 100.

The plurality of channels 200 may be formed of at least one of Ag, AgCl, Au, Pt, or stainless steel. The configuration of the channels 200 will be described below in detail with reference to FIGS. 2 and 3.

Since a conductive material 120 is inserted inside the contact lens 100, the microcurrent formed on the upper part is induced to be applied in the direction of the contact lens 100. The contact lens 100 will be described below in detail with reference to FIGS. 4 to 6.

Figure 2:
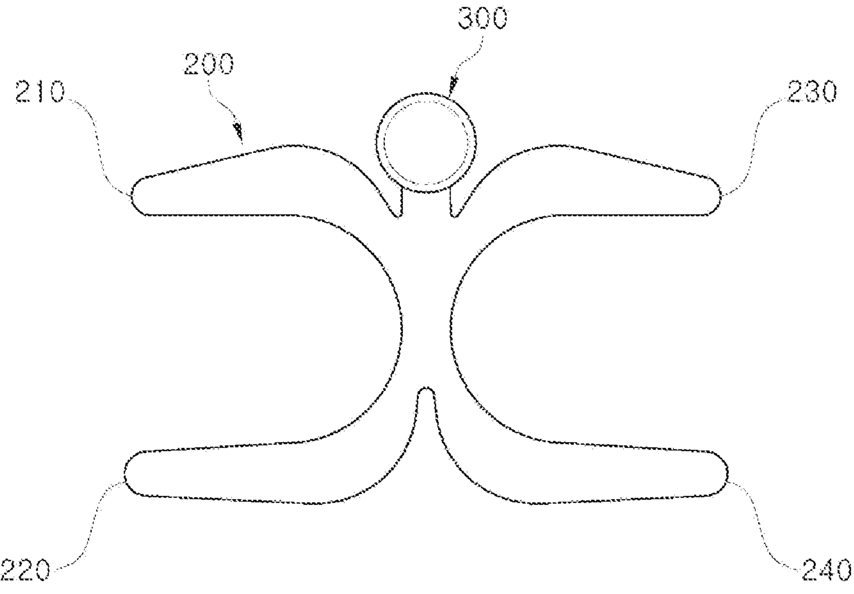
FIG. 2 illustrates the channels and signal supply unit of the device for regenerating nerve cells and suppressing immune diseases according to one embodiment of the present invention.
Figure 3:
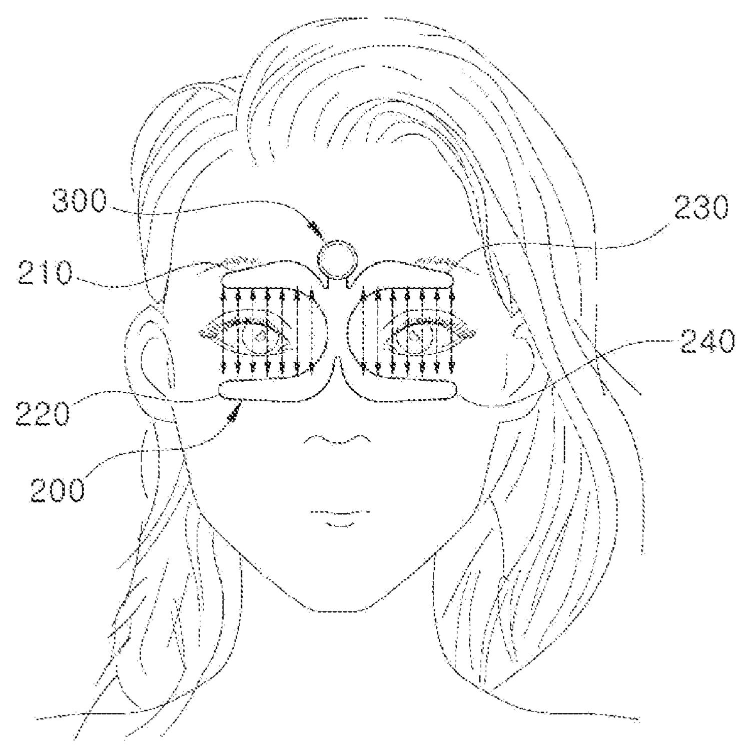
FIG. 3 shows a state wearing the device for regenerating nerve cells and suppressing immune diseases according to one embodiment of the present invention.

FIG. 2 illustrates the channels 200 and the signal supply unit 300 in the device for regenerating nerve cells and suppressing immune diseases according to one embodiment of the present invention, and FIG. 3 shows a state wearing the device for regenerating nerve cells and suppressing immune diseases according to one embodiment of the present invention.

Referring to FIGS. 2 and 3, the device for regenerating nerve cells and suppressing immune diseases according to one embodiment of the present invention may generally comprise an even number of the channels 200. Preferably, as shown in the figures, the device may include a total of four channels 200 (first channel 210, second channel 220, third channel 230, and fourth channel 240).

The first channel 210 and the third channel 230 may be disposed above the user's eyes, and the second channel 220 and the fourth channel 240 may be disposed below the user's eyes.

According to an embodiment, electrical signals that are supplied to the first channel 210 and the third channel 230 may be different from electrical signals that are supplied to the second channel 220 and the fourth channel 240.

For example, a polarity of electrical signals that are supplied to the first channel 210 and the third channel 230 may be different from a polarity of electrical signals that are supplied to the second channel 220 and the fourth channel 240. Accordingly, a voltage difference may occur between the first channel 210 and the second channel 220 and between the third channel 230 and the fourth channel 240, thus generating a current flow.

Figure 4:
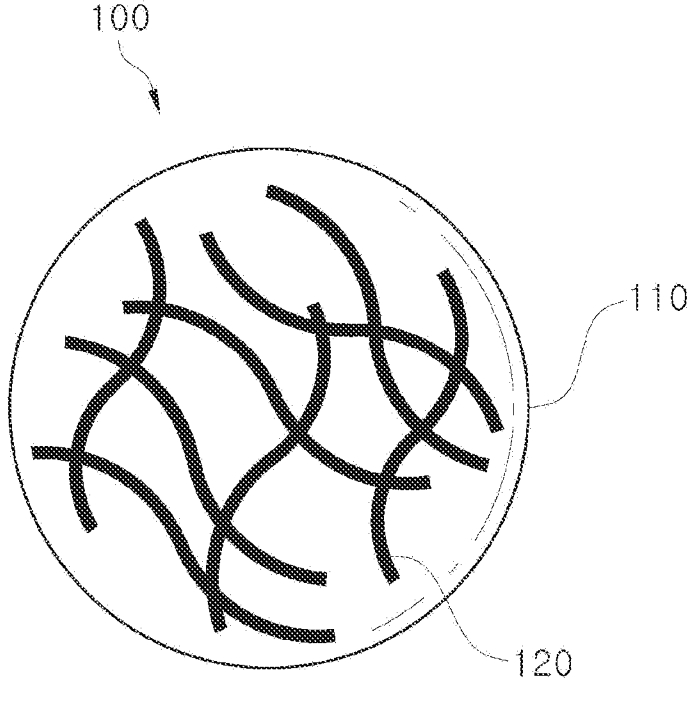
FIG. 4 illustrates the contact lens of the device for regenerating nerve cells and suppressing immune diseases according to one embodiment of the present invention.

FIG. 4 illustrates the contact lens 100 of the device for regenerating nerve cells and suppressing immune diseases according to one embodiment of the present invention.

Referring to FIG. 4, the contact lens 100 according to one embodiment of the present invention may comprise a body 110 configured to be worn on a cornea, and a conductive material 120 inserted into the body 110 and serving to induce a microcurrent generated outside the body.

The conductive material 120 refers to a material having relatively high electrical conductivity. When the conductive material 120 is present in a place where a current flows, the current will be induced to the place where the conductive material 120 is present. In this case, it is preferable that the conductive material 120 may be inserted into the body 110 in a state in which it is not in contact with the user's body, that is, the cornea.

According to an embodiment, the conductive material 120 may be composed of a plurality of conductive fibers. And, portions of the conductive material 120 composed of the plurality of conductive fibers may be in contact with each other. That is, the plurality of conductive fibers may be inserted into the body 110 of the contact lens 100 in a state in which they are in partial contact with each other.

Figure 5:
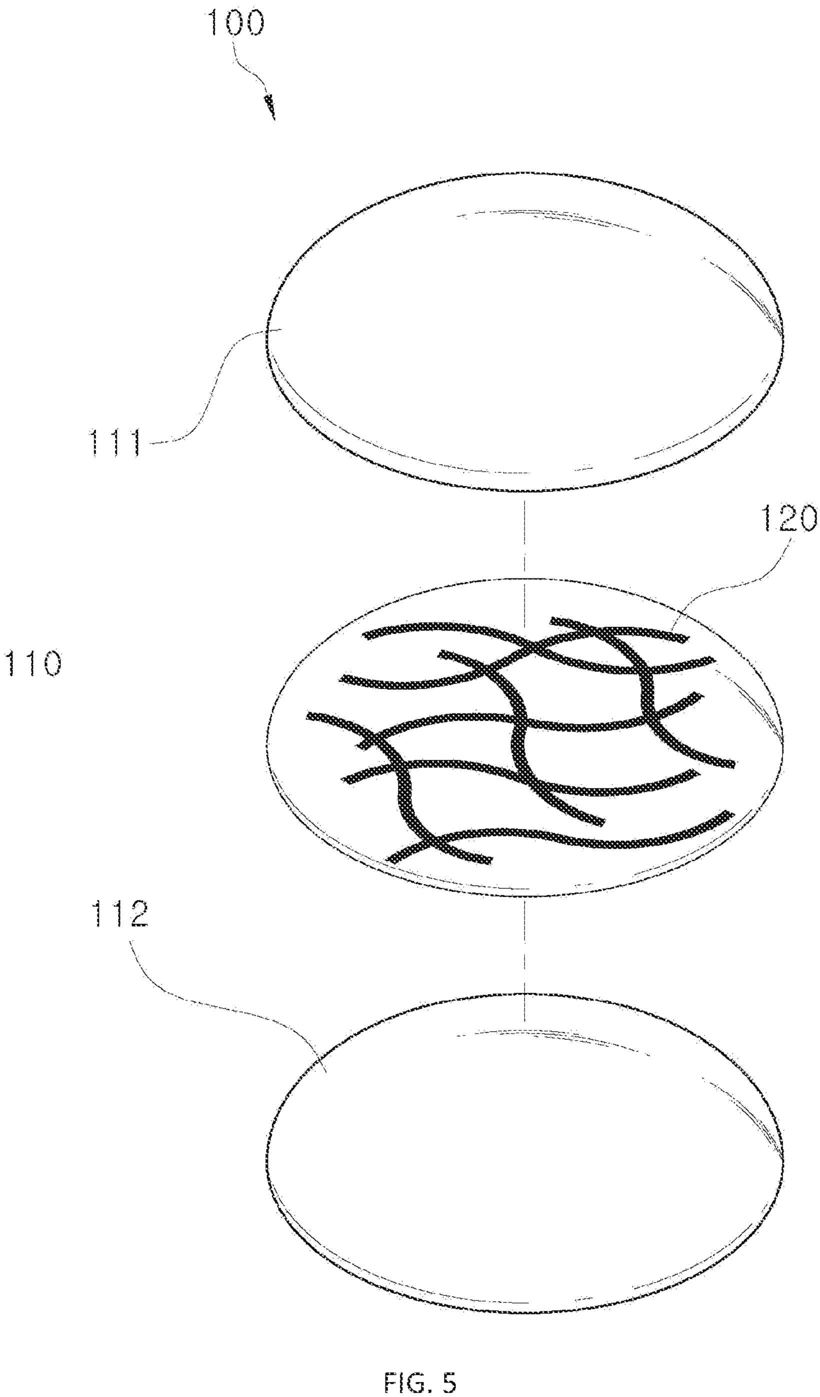
FIG. 5 is an exploded perspective view of the contact lens of the device for regenerating nerve cells and suppressing immune diseases according to one embodiment of the present invention.

FIG. 5 is an exploded perspective view of the contact lens 100 of the device for regenerating nerve cells and suppressing immune diseases according to one embodiment of the present invention.

Referring to FIG. 5, the body 110 of the contact lens 100 of the device for regenerating nerve cells and suppressing immune diseases according to one embodiment of the present invention may be composed of an upper layer 111, an intermediate layer, and a lower layer 112. And the intermediate layer is coated with fibers having conductive properties and may be formed to be disposed between the upper layer 111 and the lower layer 112.

Figure 6:
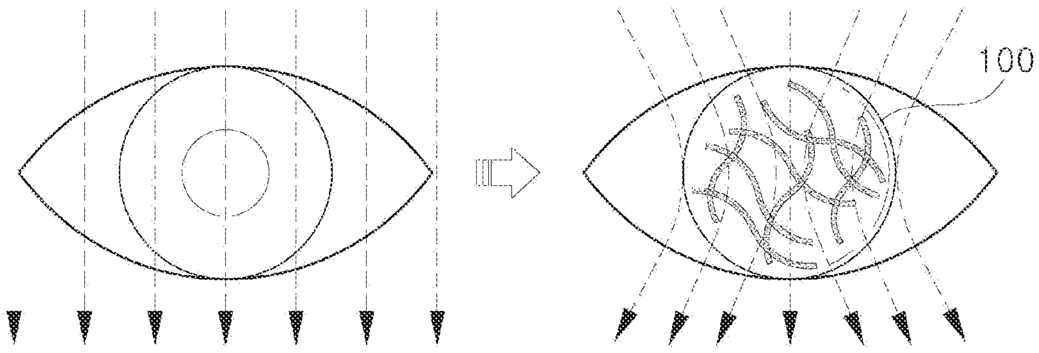
FIG. 6 shows a state in which microcurrent is induced by the contact lens of the device for regenerating nerve cells and suppressing immune diseases according to one embodiment of the present invention.

FIG. 6 shows a state in which microcurrent is induced by the contact lens 100 of the device for regenerating nerve cells and suppressing immune diseases according to one embodiment of the present invention.

Referring to FIG. 6, when the contact lens 100 containing the conductive material 120 is worn, it can be observed that the flow of microcurrent is concentrated on the cornea on which the contact lens 100 is worn.

That is, in the device for regenerating nerve cells and suppressing immune diseases according to one embodiment of the present invention, electrical signals are supplied to the channels 200 by the signal supply unit 300. And the flow of the microcurrent generated by the electrical signals supplied to the channels 200 is concentrated on the cornea on which the contact lens 100 containing the conductive material is worn.

Figure 7:
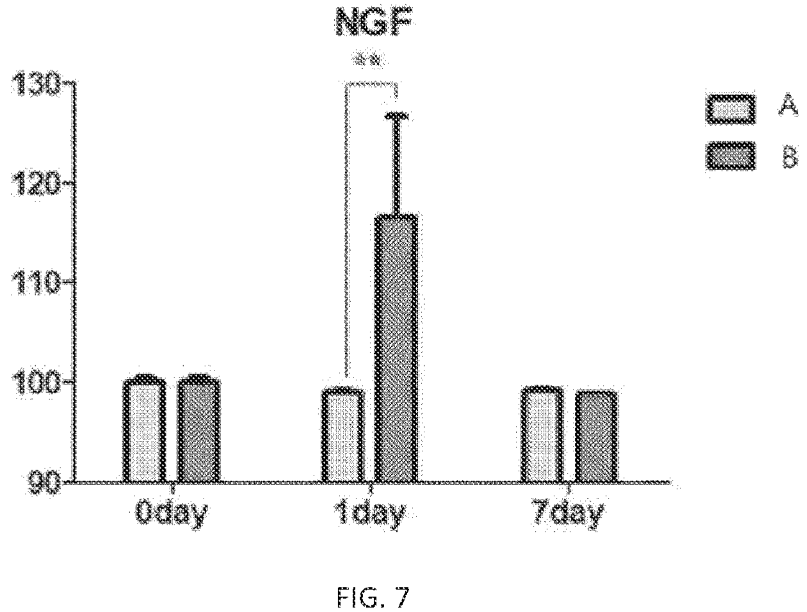
FIG. 7 is a graph showing the level of NGF expression induced by microcurrent stimulation.

FIG. 7 is a graph showing the level of NGF expression induced by microcurrent stimulation.

The graph of FIG. 7 shows the results of measuring the expression level of NGF after cutting an about 113.8-μm-thick rabbit cornea including a portion of the corneal epithelium and the upper parenchyma. In the graph, A represents an untreated control group, and B represents a group to which microcurrent was applied once daily for 30 minutes.

Referring to FIG. 7, it can be observed that the level of NGF expression is higher when microcurrent was applied than when microcurrent was not applied.

Figure 8:
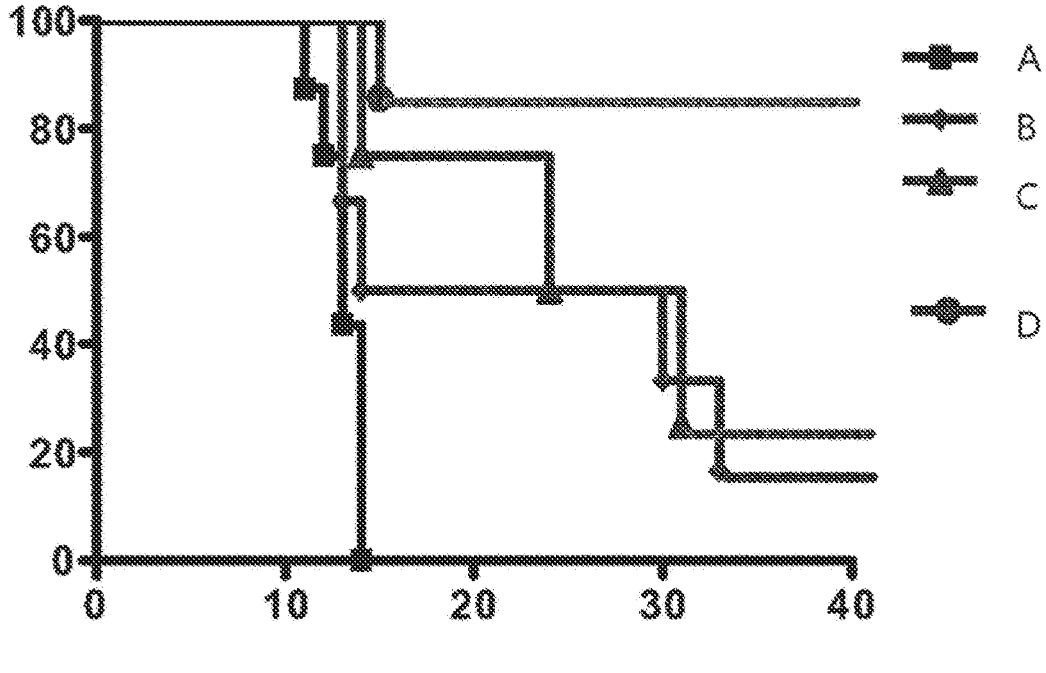
FIG. 8 is a graph showing the survival rate of transplanted corneas after corneal transplantation surgery through NGF administration.

FIG. 8 is a graph showing the survival rate of transplanted corneas after corneal transplantation surgery through NGF administration.

The graph of FIG. 8 is a graph showing the therapeutic effect of NGF. In the graph, A represents an untreated control group, B represents a group to which CTLA41g was administered, C represents a group to which CTLA41g and β-Gal were administered, and D represents a group to which CTLA41g and NGF were administered.

Referring to FIG. 8, when the level of NGF expression is increased, it can be observed that wound healing of damaged corneal tissues such as neurotrophic keratitis or neurotrophic ulcers, occurs smoothly. Additionally, modulating immune activity is improved, the survival rate of transplanted corneas after corneal allotransplantation [33] is getting higher.

The above description of the present invention is exemplary, and those of ordinary skill in the art will appreciate that the present invention can be easily modified into other specific forms without departing from the technical spirit or essential characteristics of the present invention. Therefore, it should be understood that the embodiments described above are exemplary in all aspects and are not restrictive. For example, each component described to be of a single type can be implemented in a distributed manner. Likewise, components described to be distributed can be implemented in a combined manner.

The scope of the present invention is defined by the following claims rather than by the detailed description of the invention. It shall be understood that all modifications and embodiments conceived from the meaning and scope of the claims and their equivalents fall within the scope of the present invention.

The invention claimed is:

1. A device for regenerating nerve cells and suppressing immune diseases, the device comprising:

a contact lens comprising a body configured to be worn on a cornea, and a conductive material inserted into the body and serving to induce a microcurrent generated outside the body, wherein the body is comprised of an upper layer, an intermediate layer, and a lower layer, and wherein the intermediate layer is disposed between the upper layer and the lower layer and wherein the conductive material comprises a plurality of conductive fibers each disposed on and at least partially coplanar with a surface of the intermediate layer;

a plurality of channels configured to come into close contact with skins around a user's eyes and to generate a flow of microcurrent on the upper layer of the contact lens worn over each of the user's eyes; and a signal supply unit configured to supply electrical signals to the plurality of channels;

wherein when the plurality of channels generate the flow of microcurrent on the upper layer of the contact lens the plurality of conductive fibers of the intermediate layer are adapted to concentrate the flow of microcurrent on the cornea.

2. The device according to claim 1, wherein the plurality of conductive fibers are in partial contact with each other.

3. The device according to claim 1, wherein the plurality of channels comprise:

first and third channels configured to be disposed above the user's eyes; and second and fourth channels configured to be disposed under the user's eyes, wherein electrical signals that are supplied to the first and third channels are different from electrical signals that are supplied to the second and fourth channels.

4. The device according to claim 1, wherein the electrical signals are standardized pulse signals.

5. The device according to claim 4, wherein the standardized pulse signals are pulse waves that are applied at intervals of 500 ms.

6. The device according to claim 3, wherein a polarity of the electrical signals that are supplied to the first and third channels are different from a polarity of the electrical signals that are supplied to the second and fourth channels to generate the flow of microcurrent between the first and second channels and between the third and fourth channels.

7. The device according to claim 3, wherein a voltage of the electrical signals that are supplied to the first and third channels are different from a voltage of the electrical signals that are supplied to the second and fourth channels to generate the flow of microcurrent between the first and second channels and between the third and fourth channels.

8. The device according to claim 1, wherein at least two of the plurality of conductive fibers are in partial overlapping contact with each other.

* * * * *